(12) United States Patent
Loomas et al.

(10) Patent No.: US 7,422,584 B2
(45) Date of Patent: Sep. 9, 2008

(54) EXTRAPLEURAL AIRWAY DEVICE AND METHOD

(75) Inventors: Bryan Loomas, Los Gatos, CA (US); Gary Kaplan, San Francisco, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 511 days.

(21) Appl. No.: 10/615,491

(22) Filed: Jul. 7, 2003

(65) Prior Publication Data

US 2004/0211434 A1    Oct. 28, 2004

Related U.S. Application Data

(60) Provisional application No. 60/393,964, filed on Jul. 5, 2002.

(51) Int. Cl.
   *A61B 18/18* (2006.01)
(52) U.S. Cl. ................. 606/32; 128/898; 623/23.64
(58) Field of Classification Search ............ 606/27–52, 606/2–3, 7, 10; 128/898; 623/23.64, 23.65
   See application file for complete search history.

(56) References Cited

U.S. PATENT DOCUMENTS

| | | | |
|---|---|---|---|
| 3,617,060 A | 11/1971 | Leggi | |
| 4,622,968 A * | 11/1986 | Persson | 604/165.01 |
| 6,231,587 B1 * | 5/2001 | Makower | 606/198 |
| 6,493,589 B1 * | 12/2002 | Medhkour et al. | 607/99 |
| 6,629,951 B2 * | 10/2003 | Laufer et al. | 604/96.01 |
| 6,692,494 B1 * | 2/2004 | Cooper et al. | 606/46 |
| 6,749,606 B2 * | 6/2004 | Keast et al. | 606/41 |
| 6,886,558 B2 | 5/2005 | Tanaka | |
| 7,086,398 B2 | 8/2006 | Tanaka | |
| 2002/0042564 A1 | 4/2002 | Cooper et al. | |
| 2002/0042565 A1 | 4/2002 | Cooper et al. | |
| 2002/0049370 A1 | 4/2002 | Laufer et al. | |
| 2004/0073201 A1 | 4/2004 | Cooper et al. | |
| 2005/0049615 A1 | 3/2005 | Cooper et al. | |
| 2005/0085801 A1 | 4/2005 | Cooper et al. | |
| 2005/0096529 A1 | 5/2005 | Cooper et al. | |

(Continued)

OTHER PUBLICATIONS

Flenley, D., et al., "Factors Affecting Gas Exchange by Collateral Ventilation in the Dog," *Respiration Physiology*, 15:52-69, 1972.

(Continued)

*Primary Examiner*—Roy D. Gibson
*Assistant Examiner*—Pete J Vrettakos
(74) *Attorney, Agent, or Firm*—Levine Bagade Han LLP

(57) ABSTRACT

This is directed to improving the gaseous exchange in a lung of an individual and particularly, this is directed to improving the gaseous exchange in individuals having chronic obstructive pulmonary disease. It generally includes fluidly connecting the lung to an extrapleural airway such as the trachea. In one variation, a conduit is deployed to place the lung and the trachea in fluid communication which allows trapped oxygen-reduced air to pass directly out of the lung and into the trachea. Removing nonfunctional air from the lung tends to improve the gaseous exchange of oxygen into the blood and decompress hyper-inflated lungs. Sealant and biocompatible adhesives may be provided on the exterior of the conduit to prevent side flow, leaks and to otherwise prevent air from entering spaces not intended to receive air such as the pleura space.

24 Claims, 14 Drawing Sheets

U.S. PATENT DOCUMENTS

2006/0276807 A1    12/2006    Keast et al.

OTHER PUBLICATIONS

Hogg, W., et al., "Gas Diffusion Across Collateral Channels," *Journal of Applied Physiology,* 33(5):568-575.

Macklem, P., "Collateral ventilation," *The New England Journal of Medicine.,* 298(1):49-50, 1978.

Menkes, H., et al., "Influence of Surface Forces on Collateral Ventilation," *Journal of Applied Physiology,* 31(4):544-549, 1971.

Terry, P., et al., "Collateral Ventilation in Man," *The New England Journal of Medicine,* 298(1):10-15, 1978.

Woolcock, A., et al., "Mechanical Factors Influencing Collateral Ventilation in Human, Dog and Pig Lungs," *Journal of Applied Physiology,* 30(1):99-115, 1971.

* cited by examiner

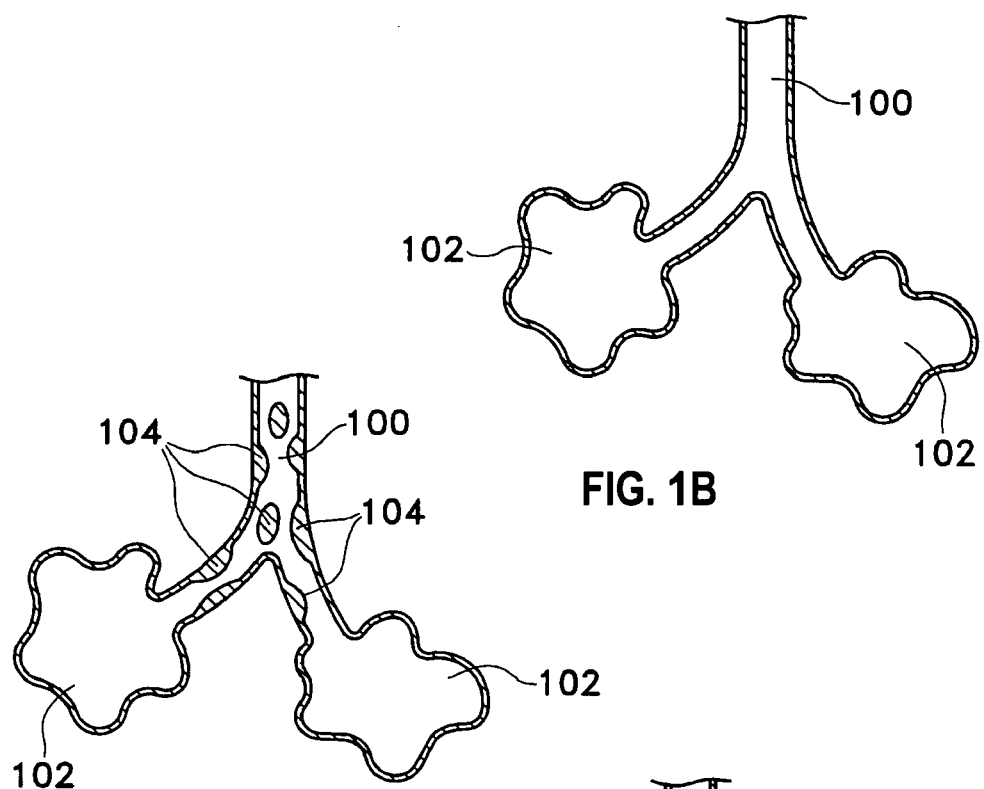
FIG. 1B
FIG. 1C
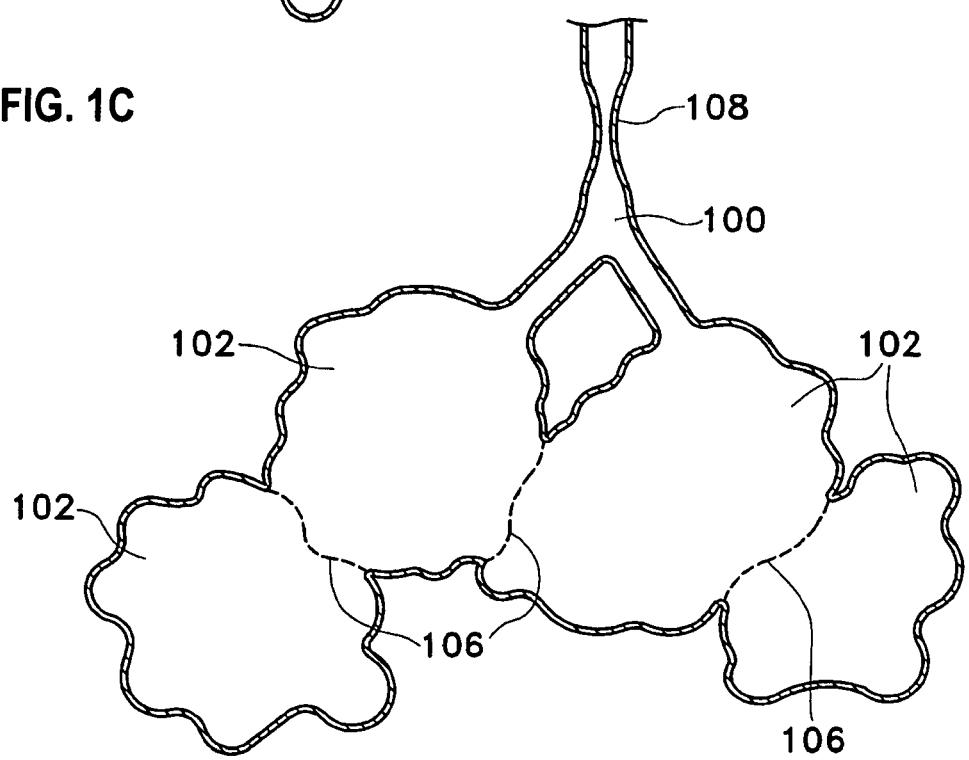
FIG. 1D

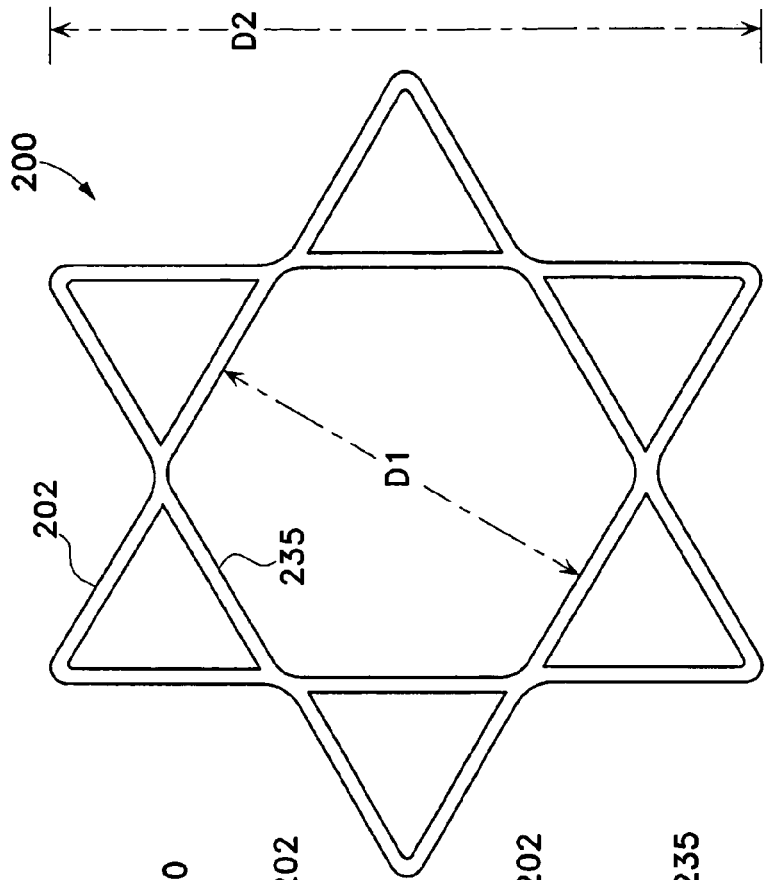
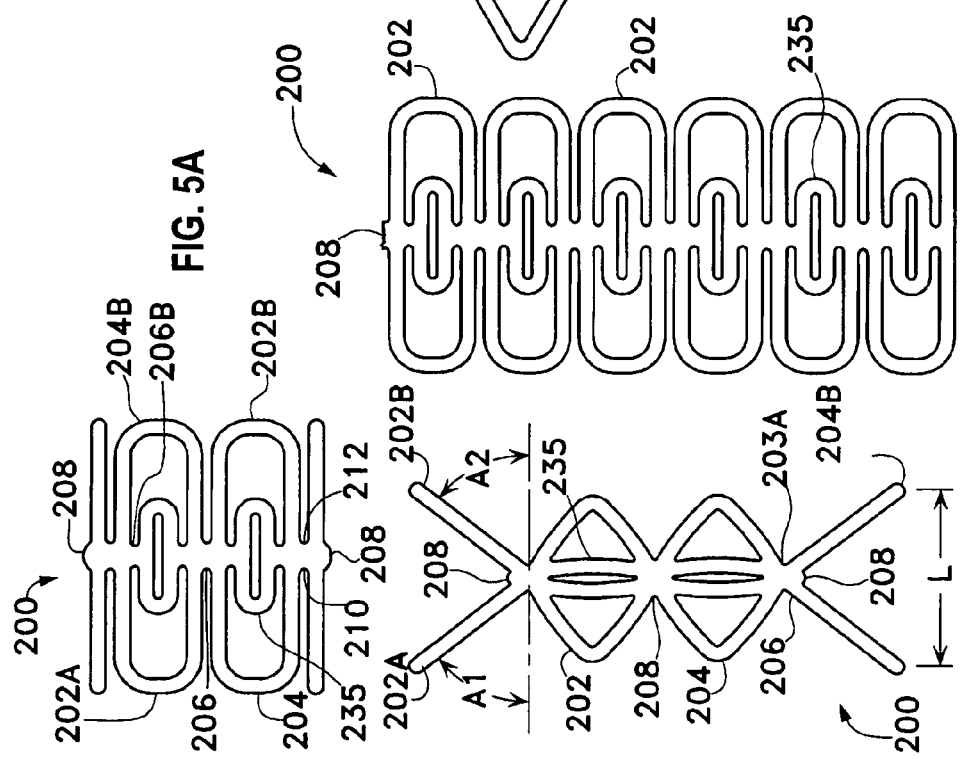
FIG. 5C
FIG. 5A
FIG. 5B
FIG. 6

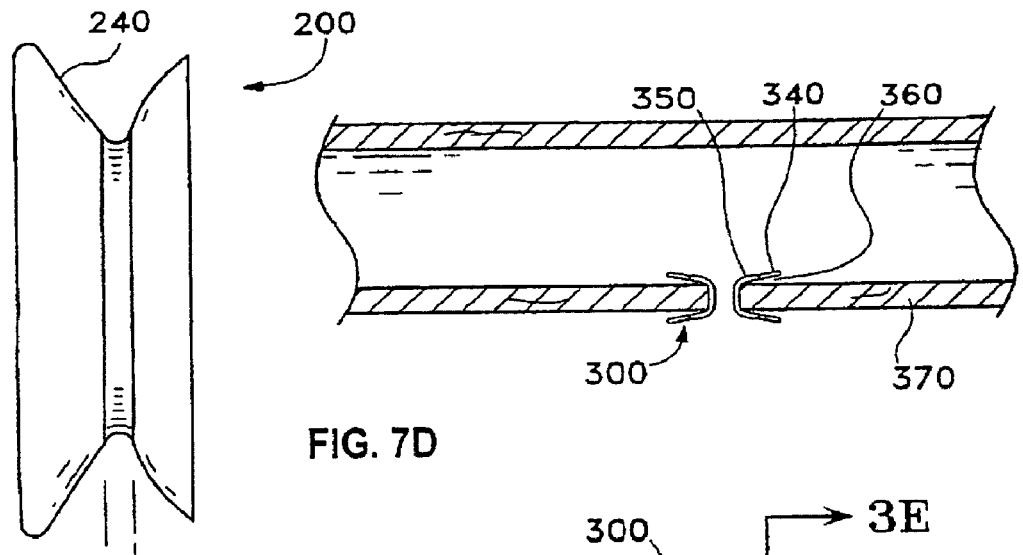
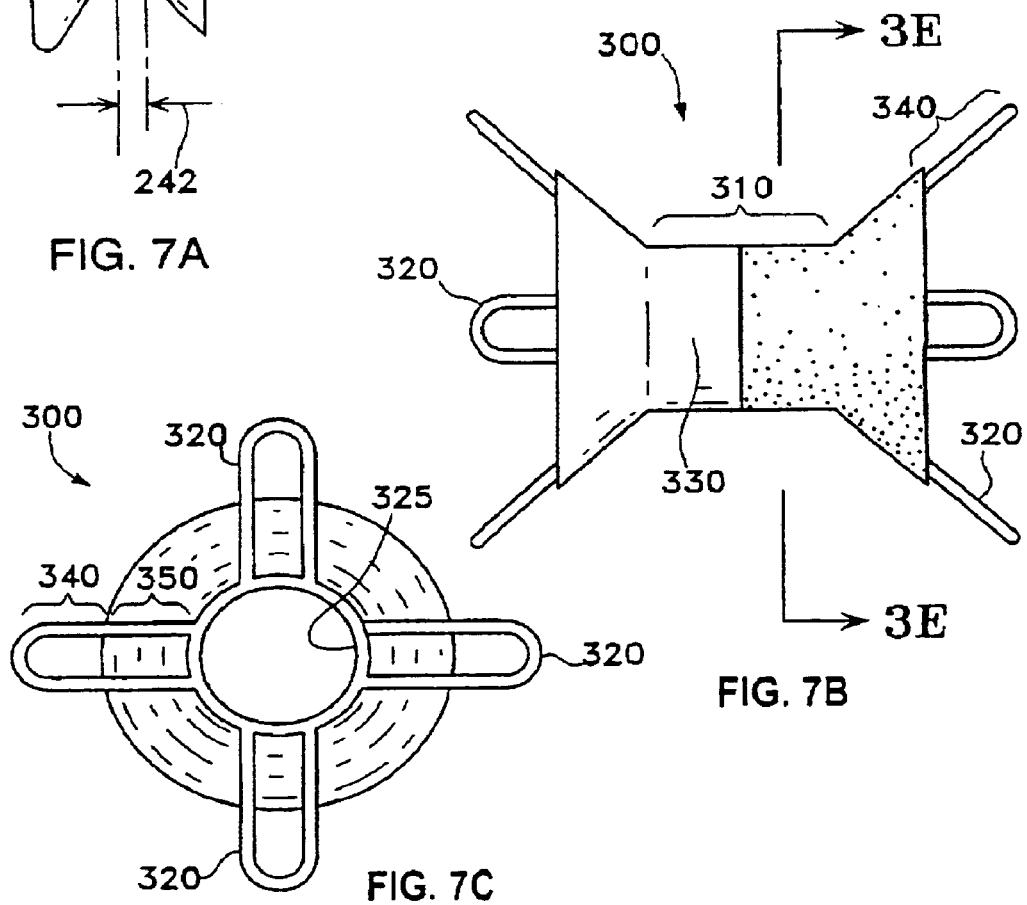
FIG. 7A
FIG. 7B
FIG. 7C
FIG. 7D

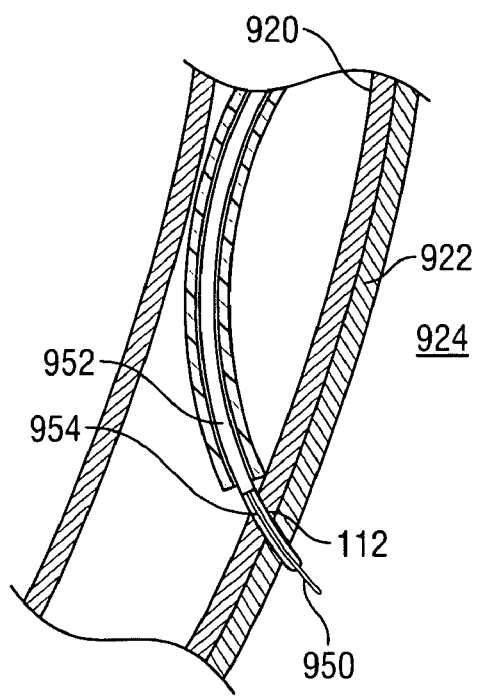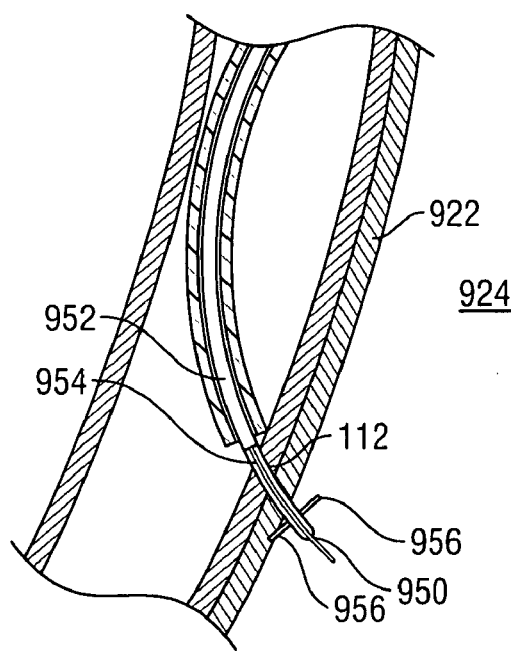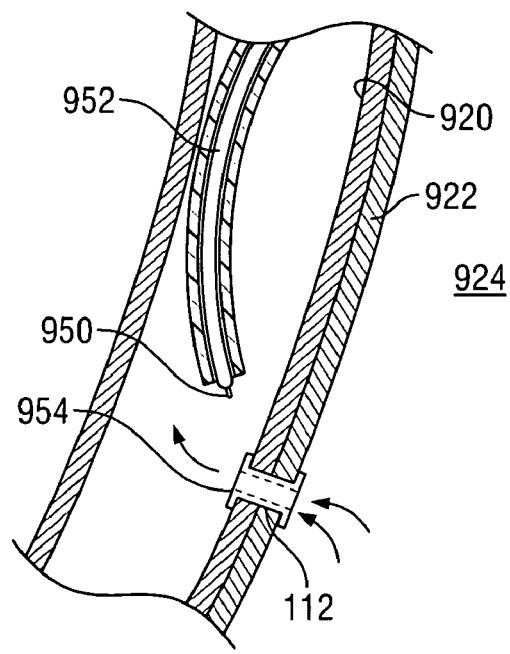
FIG. 9E
FIG. 9F
FIG. 9G

EXTRAPLEURAL AIRWAY DEVICE AND METHOD

REFERENCE TO PRIOR APPLICATIONS

This application claims benefit of 60/393,964 Jul. 5, 2002.

FIELD OF THE INVENTION

This is directed to improving the gaseous exchange in a lung of an individual and more particularly, this is directed to improving the gaseous exchange in a lung of an individual having chronic obstructive pulmonary disease.

BACKGROUND OF THE INVENTION

In 1995, the American Lung Association (ALA) estimated that between 15-16 million Americans suffered from chronic obstructive pulmonary disease (COPD) which includes diseases such as chronic bronchitis, emphysema, and some types of asthma. The ALA estimated that COPD was the fourth-ranking cause of death in the U.S. The ALA estimates that the rates of emphysema is 7.6 per thousand population, and the rate for chronic bronchitis is 55.7 per thousand population.

Those inflicted with COPD face disabilities due to the limited pulmonary functions. Usually, individuals afflicted by COPD also face loss in muscle strength and an inability to perform common daily activities. Often, those patients desiring treatment for COPD seek a physician at a point where the disease is advanced. Since the damage to the lungs is irreversible, there is little hope of recovery. Most times, the physician cannot reverse the effects of the disease but can only offer treatment and advice to halt the progression of the disease.

To understand the detrimental effects of COPD, the workings of the lungs requires a cursory discussion. The primary function of the lungs is to permit the exchange of two gasses by removing carbon dioxide from arterial blood and replacing it with oxygen. Thus, to facilitate this gaseous exchange, the lungs provide a blood gas interface. The oxygen and carbon dioxide move between the gas (air) and blood by diffusion. This diffusion is possible since the blood is delivered to one side of the blood-gas interface via small blood vessels (capillaries). The capillaries are wrapped around numerous air sacs called alveoli which function as the blood-gas interface. A typical human lung contains about 300 million alveoli.

The air is brought to the other side of this blood-gas interface by a natural respiratory airway, hereafter referred to as a natural airway or airway, consisting of branching tubes which become narrower, shorter, and more numerous as they penetrate deeper into the lung. As shown in FIG. 1A, the trachea 10 branches into the right bronchi (not shown) and left bronchi 20 which divide into lobar, then segmental bronchi. The left bronchi 20 is shown branching into secondary bronchi 24 each of which further divides into tertiary bronchi 30. Ultimately, the branching continues down to the bronchioles 100 and terminal bronchioles 40 which lead to the alveoli (not shown). Plates of cartilage may be found as part of the walls throughout most of the airways from the trachea to the bronchi. The cartilage plates become less prevalent as the airways branch. Eventually, in the last generations of the bronchi, the cartilage plates are found only at the branching points. The bronchi and bronchioles may be distinguished as the bronchi lie proximal to the last plate of cartilage found along the airway, while the bronchiole lies distal to the last plate of cartilage. The bronchioles 100 are the smallest airways that do not contain alveoli. The function of the bronchi and bronchioles is to provide conducting airways that lead air to and from the gas-blood interface. However, these conducting airways do not take part in gas exchange because they do not contain alveoli. Rather, the gas exchange takes place in the alveoli which are found in the distal-most end of the airways.

Breathing involves the lungs, the rib cage, the diaphragm and abdominal wall. During inspiration, inspiratory muscles contract increasing the volume of the chest cavity. As a result of the expansion of the chest cavity, the pleural pressure, the pressure within the chest cavity, becomes sub-atmospheric. Consequently, air flows into the lungs and the lungs expand. During unforced expiration, the inspiratory muscles relax and the lungs begin to recoil and reduce in size. The lungs recoil because they contain elastic fibers that allow for expansion, as the lungs inflate, and relaxation, as the lungs deflate, with each breath. This characteristic is called elastic recoil. The recoil of the lungs causes alveolar pressure to exceed atmospheric pressure causing air to flow out of the lungs and deflate the lungs. 'If the lungs' ability to recoil is damaged, the lungs cannot contract and reduce in size from their inflated state. As a result, the lungs cannot evacuate all of the inspired air.

In addition to elastic recoil, the lung's elastic fibers also assist in keeping small airways open during the exhalation cycle. This effect is also known as "tethering" of the airways. Such tethering is desirable since small airways do not contain cartilage that would otherwise provide structural rigidity for these airways. Without tethering, and in the absence of structural rigidity, the small airways collapse during exhalation and prevent air from exiting thereby trapping air within the lung.

Emphysema is characterized by irreversible biochemical destruction of the alveolar walls that contain the elastic fibers, called elastin, described above. The destruction of the alveolar walls results in a dual problem of reduction of elastic recoil and the loss of tethering of the airways. Unfortunately for the individual suffering from emphysema, these two problems combine to result in extreme hyperinflation (air trapping) of the lung and an inability of the person to exhale. In this situation, the individual will be debilitated since the lungs are unable to perform gas exchange at a satisfactory rate.

One further aspect of alveolar wall destruction is that the airflow between neighboring air sacs, known as collateral ventilation or collateral air flow, is markedly increased as when compared to a healthy lung. While alveolar wall destruction decreases resistance to collateral ventilation, the resulting increased collateral ventilation does not benefit the individual since air is still unable to flow into and out of the lungs. Hence, because this trapped air is rich in $CO_2$, it is of little or no benefit to the individual.

Chronic bronchitis is characterized by excessive mucus production in the bronchial tree. Usually there is a general increase in bulk (hypertrophy) of the large bronchi and chronic inflammatory changes in the small airways. Excessive amounts of mucus are found in the airways and semisolid plugs of this mucus may occlude some small bronchi. Also, the small airways are usually narrowed and show inflammatory changes.

Currently, although there is no cure for COPD, treatment includes bronchodilator drugs, and lung reduction surgery. The bronchodilator drugs relax and widen the air passages thereby reducing the residual volume and increasing gas flow permitting more oxygen to enter the lungs. Yet, bronchodilator drugs are only effective for a short period of time and require repeated application. Moreover, the bronchodilator drugs are only effective in a certain percentage of the population of those diagnosed with COPD. In some cases, patients suffering from COPD are given supplemental oxygen to assist in breathing. Unfortunately, aside from the impracticalities of needing to maintain and transport a source of oxygen for everyday activities, the oxygen is only partially functional and does not eliminate the effects of the COPD. Moreover, patients requiring a supplemental source of oxygen are usually never able to return to functioning without the oxygen.

Lung volume reduction surgery is a procedure which removes portions of the lung that are over-inflated. The improvement to the patient occurs as a portion of the lung that remains has relatively better elastic recoil which allows for reduced airway obstruction. The reduced lung volume also improves the efficiency of the respiratory muscles. However, lung reduction surgery is an extremely traumatic procedure which involves opening the chest and thoracic cavity to remove a portion of the lung. As such, the procedure involves an extended recovery period. Hence, the long term benefits of this surgery are still being evaluated. In any case, it is thought that lung reduction surgery is sought in those cases of emphysema where only a portion of the lung is emphysematous as opposed to the case where the entire lung is emphysematous. In cases where the lung is only partially emphysematous, removal of a portion of emphysematous lung which was compressing healthier portions of the lung allows the healthier portions to expand, increasing the overall efficiency of the lung. If the entire lung is emphysematous, however, removal of a portion of the lung removes gas exchanging alveolar surfaces, reducing the overall efficiency of the lung. Lung volume reduction surgery is thus not a practical solution for treatment of emphysema where the entire lung is diseased.

Both bronchodilator drugs and lung reduction surgery fail to capitalize on the increased collateral ventilation taking place in the diseased lung. There remains a need for a medical procedure that can alleviate some of the problems caused by COPD. There is also a need for a medical procedure that alleviates some of the problems caused by COPD irrespective of whether a portion of the lung, or the entire lung is emphysematous. The production and maintenance of collateral openings through an airway wall allows air to pass directly out of the lung tissue responsible for gas exchange. These collateral openings serve to decompress hyper-inflated lungs and/or facilitate an exchange of oxygen into the blood.

Methods and devices for creating, and maintaining collateral channels are discussed in U.S. patent application Ser. No. 09/633,651, filed on Aug. 7, 2000; U.S. patent application Ser. Nos. 09/947,144, 09/946,706, and 09/947,126 all filed on Sep. 4, 2001; U.S. Provisional Application No. 60/317,338 filed on Sep. 4, 2001; U.S. Provisional Application No. 60/334,642 filed on Nov. 29, 2001; U.S. Provisional Application No. 60/367,436 filed on Mar. 20, 2002; and U.S. Provisional Application No. 60/374,022 filed on Apr. 19, 2002; and U.S. Provisional Application No. 60/387,163, filed Jun. 7, 2002 each of which is incorporated by reference herein in its entirety.

Notwithstanding the above, a technique for improving the gaseous exchange in a lung as described herein is still desirable.

SUMMARY OF THE INVENTION

The devices and methods described herein serve to improve the gaseous exchange in the lungs. In one variation of the present invention, an extrapleural or extraparenchymal airway such as the trachea is fluidly connected to the lung with a conduit. The conduit includes a first end portion, a second end portion and a passageway extending between the end portions. The end portions are adapted to secure the conduit to the tissue structures such that the extrapleural airway is in direct fluid communication with the lung.

In one variation a method for improving gas exchange in the lung comprises creating a channel in each of the extrapleural airway wall and the lung or pleural wall prior to the step of fluidly connecting the trachea to the lung. The surgically created channels or openings may be created with an instrument that emits energy such as radio frequency energy. Once the channel(s) are created in the tissue walls, a conduit may be deployed to provide a passageway for trapped air to flow directly from the lung and into the trachea.

The method may also comprise the step of fixing the extra pleural airway wall to the pleural membrane of the lung prior to creating the channel therethrough. The step of fixing may be performed by deploying an adhesive between the wall and membrane. Also, the step of fixing may be performed by deploying a tissue fastener. The tissue fastener may comprise a body which extends through the wall and the membrane. The tissue fastener has two end portions which are adapted to hold the wall and the membrane together.

In another variation, the conduit includes a center section and deflectable extension members wherein the opposing extension members may be deflected to sandwich tissue therebetween. Other variations include conduits having various shapes and coatings. In one variation, the conduit includes an extended center section having a length of upwards of 5 mm.

The inventive method may also include the step of delivering a sealant with the conduit. The sealant may be disposed on the exterior of the conduit. The sealant may also be delivered separate from the conduit. The sealant serves to secure the conduit in place, hold the tissues together, prevent side flow around the conduit, and perhaps affect the wound healing response of the tissue to decrease the likelihood that the conduit will be ejected.

Other aspects of the invention will become apparent upon reading the following detailed description in combination with the corresponding figures and the appended claims.

BRIEF DESCRIPTION OF THE DRAWINGS

FIGS. 1B-1D illustrate various states of the natural airways and the blood-gas interface.

FIG. 5A illustrates a side view of an expandable conduit in an undeployed state.

FIG. 5B illustrates a side view of the conduit of FIG. 5A shown in a deployed shape.

FIG. 5C illustrates a front view of the conduit shown in FIG. 5B.

FIG. 6 is a cylindrical projection of the undeployed conduit shown in FIG. 5A.

FIG. 7A illustrates a side view of another conduit having a tissue barrier in a deployed state.

FIG. 7B illustrates a side view of another conduit having a tissue barrier.

FIG. 7C is a front view of the conduit shown in FIG. 7B.

FIG. 7D illustrates a conduit positioned in a channel created in a tissue wall.

FIGS. 9A-9G illustrate a method for deploying the conduit.

DETAILED DESCRIPTION OF THE INVENTION

Described herein are methods and devices for improving the gaseous exchange in a lung. More particularly, a method is described for improving the gaseous exchange in a lung of an individual having chronic obstructive pulmonary disease. The inventive method generally includes fluidly connecting the lung with an extrapleural airway such as the trachea using a conduit. Once the tissue structures are in fluid communication, gas may flow or pass directly from the parenchymal tissue of the lung to the extrapleural airway such as the trachea via the deployed conduit. By "pass directly" from the lung to the extrapleural airway it is meant that at least some volume of gas flows direct from the inner tissue of the lung to the extrapleural airway without passing through typical flow pathways such as the bronchioles, bronchus, etc. which may be constricted or otherwise flow-resistant. Also, by "extrapleural airway" it is meant any airway or portion of an airway that is outside of the pleura such as, for example, the trachea or mainstem bronchus. Furthermore, it is intended that in any embodiment described herein, the created path may pass through other tissues that are located between the extrapleural airway and pleura. Furthermore, the invention may include creating intra-lung airflow, e.g., between separate lobes of the lung while passing through the pleural surfaces of the lobes.

Figure 1A:
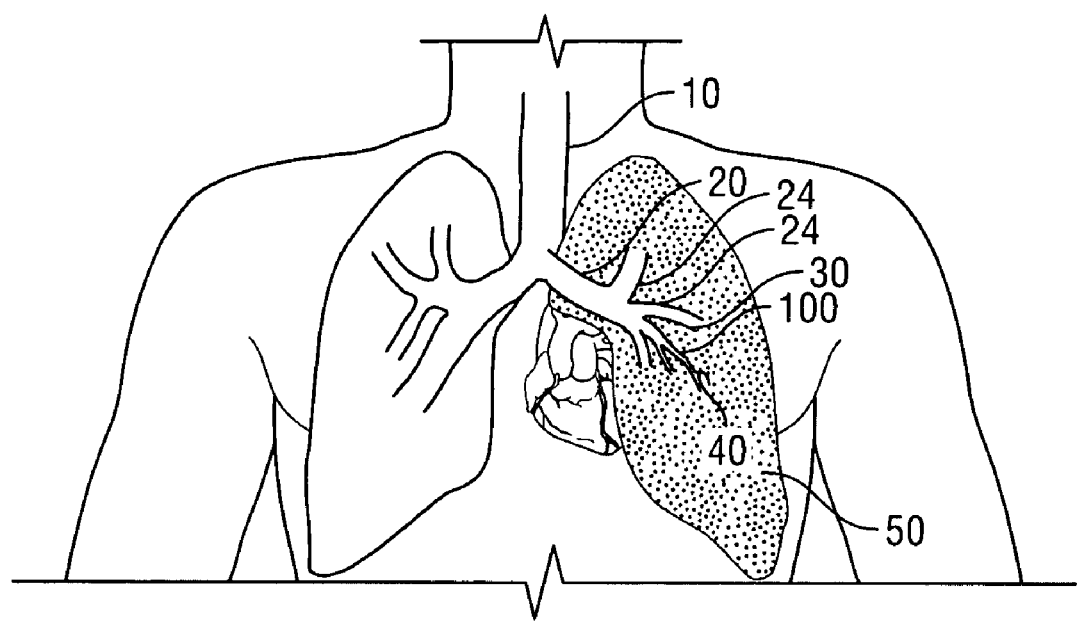
FIG. 1A illustrates the lungs and the airways used to transport air to and from the blood-gas interface in the lungs.

FIGS. 1B-1D are simplified illustrations of various states of an airway and the blood gas interface. In particular, FIG. 1B shows a natural airway 100 which eventually branches to a blood gas interface 102. FIG. 1C illustrates an airway 100 and blood gas interface 102 in an individual having COPD. The obstructions 104 impair the passage of gas between the airways 100 and the interface 102. FIG. 1D illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. A combination of the phenomena depicted in FIGS. 1C-1D may exist in the same lung and lead to inspired air remaining trapped inside the lung. Inspired air may be depleted of oxygen and occupy space in the parenchymal tissue of the lung (see e.g., reference numeral 50 of FIG. 1A). It is therefore desirable to create the flow pathways described herein which allow the inspired air to flow directly out of the lung bypassing the obstructed airways. Ridding the lung of the nonfunctional air allows the healthy portions of the lung to expand to a greater volume, improving the gaseous exchange.

Figure 2A:
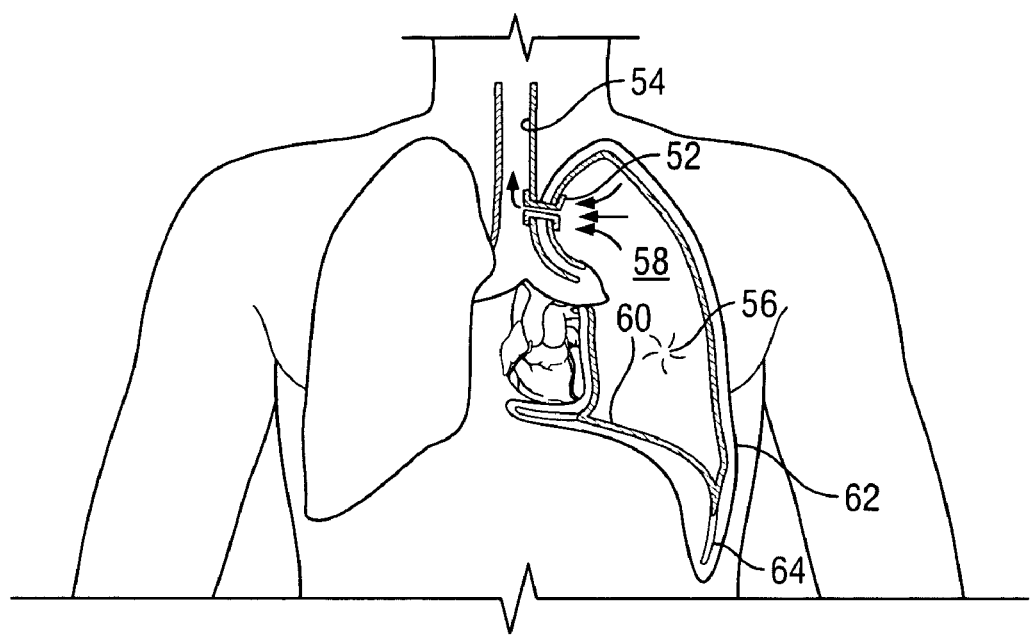
FIG. 2A is a schematic illustration of a conduit fluidly connecting the left lung to the trachea.

FIG. 2A illustrates a technique for fluidly connecting an extrapleural airway to the lung. In particular, a conduit 52 is shown connecting the trachea 54 to parenchymal tissue within the left lung 58. The conduit includes a passageway that extends through three layers of tissue including the visceral pleura 60, parietal pleura 62, and the trachea wall 54.

Figure 2B:
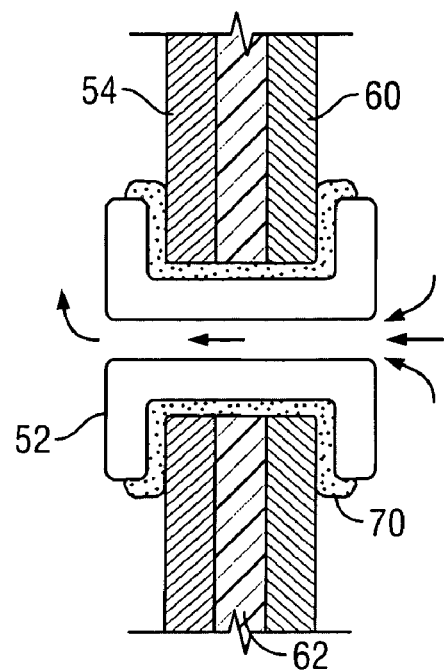
FIG. 2B is an enlarged cross sectional view of the deployed conduit shown in FIG. 2A.

The conduit 52 shown in FIG. 2B is grommet shaped and its end portions are adapted to secure the conduit in place and hold the tissue walls together. FIG. 2B additionally shows a sealant 70 in the spaces between the exterior of the conduit and the edges of the tissue walls defining the channel. The sealant may serve one or more functions including securing and sealing the conduit in place. For example, the sealant may comprise an adhesive material which secures the walls and the conduit together. Also, the sealant may block leaks and side flow of air around the conduit. Leakage around the conduit is undesirable because the air may enter the chest cavity or pleural space 64. This may lead to pneumothorax or pneumomediastinum each of which is undesirable. Also, the sealant material may be a bioactive agent that, for example, encourages fibrotic wound healing. Examples of various sealant and agents include cyanoacrylate, fibrin glue, talc, and substances comprising talc. However, other substances may be employed. Also, as described herein, the structure or shape of the conduit itself may serve to prevent side flow and leaks as well as provide a passageway for air to flow through.

The present invention may also include the step of fixing or stabilizing the extrapleural airway wall and the pleural membrane tissue layers at a selected or target region. Fixing these tissue layers together prior to creating the channel through the layers can lessen the likelihood that air will enter the pleural space. Indeed, the lung may collapse if air enters the pleural space.

Figure 2C:
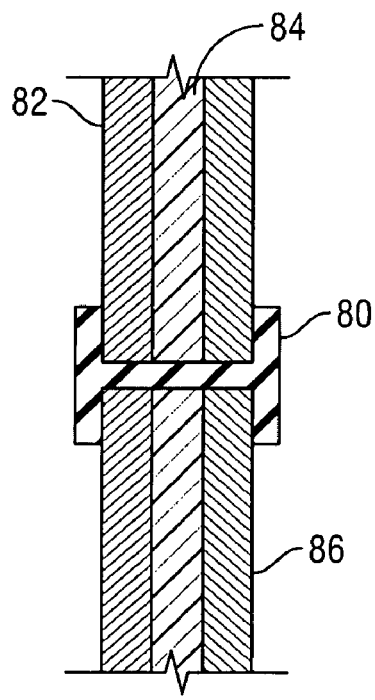
FIG. 2C is an enlarged view of an extrapleural airway wall fixed to a pleural membrane layer(s) using a tissue fastener element.

The tissues may be fixed using various techniques. For example, an adhesive or tissue sealant may be injected into the tissue at the target location prior to creating the channels. Also, as shown in FIG. 2C a tissue fastener element 80 may be deployed through the tissue layers 82, 84, 86 such that the tissue layers are fixed and stabilized prior to creating the channel for the conduit (not shown). The channel may be created adjacent the fastener element 80. The tissue fastener may be made of a biocompatible material such as the materials used for the conduit. The tissue fastener may include a body and two enlarged end portions. The end portions shall be large enough such that the tissue layers are held together. Also, once the step of creating the channel is completed and a conduit is deployed, the fixing mechanism such as the tissue fastener may be removed because the conduit holds the tissues together. Alternatively, the tissue fastener may be left in place after the conduit is deployed.

Still other techniques may be employed to affix the parietal pleura to the visceral pleura such as heating, melting and coagulating devices. An electrode or heating element may be positioned at the target region and energy may be sent to the tissue layers causing the tissue layers to coagulate together. This fixing step may be performed 1 day or more in advance of creating the channels through the tissue layers.

Additionally, it is contemplated that during the procedures described herein the lung opposite the lung being treated may be isolated and ventilated such that the lung being treated is not used to carry out gaseous exchange during the procedure.

Figure 3:
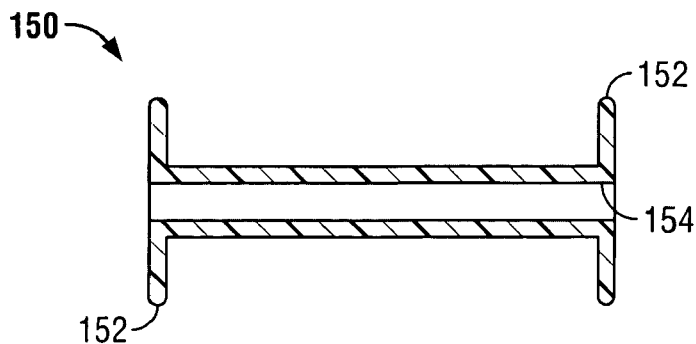
FIG. 3 is a cross sectional view of a grommet shaped conduit.

FIGS. 3 and 4 respectively illustrate conduits 150, 160 having a body or center section extending between two enlarged end portions 152, 162. An open passageway 154, 164 extends from one end to the other.

The conduit in FIG. 3 is grommet shaped. A conduit of this type may be made of a plastic or metal. For example, the conduit may be a biocompatible rubber which is squeezed into position within a surgically created channel extending through the tissue walls. By "channel" it is meant to include but not be limited to any opening, hole, slit, channel or passage created in an airway wall. The channel may be created in tissue having a discrete wall thickness and the channel may extend all the way through the wall. Also, a channel may extend through lung tissue which does not have well defined boundaries such as, for example, parenchymal tissue.

In any event, when conduit 150 is positioned in such a channel, the enlarged end portions 152 hold the tissue walls together and tend to prevent side flow (or leakage) around the conduit. Additionally, the conduit may be selected such that it is slightly oversized relative to the channel in which it is placed. The exterior of the conduit will thus press against the edges of the tissue walls eliminating side spaces for air to enter.

Figure 4A:
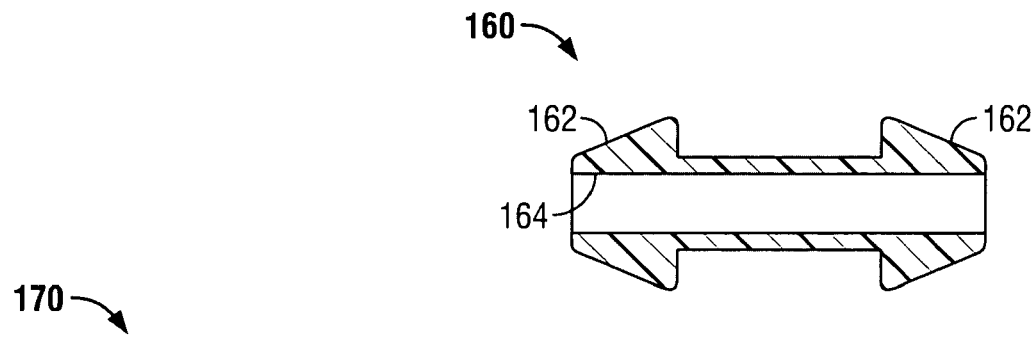
FIGS. 4A-4C are cross sectional views of other types of conduits.

FIG. 4A illustrates another grommet shaped conduit having tapered end portions 162. The tapered end portions serve the same purposes as those identified above. Also, the tapered end portions may make the conduit less traumatic to deploy since the tapered end portions have a gradually increasing diameter.

Figure 4B:
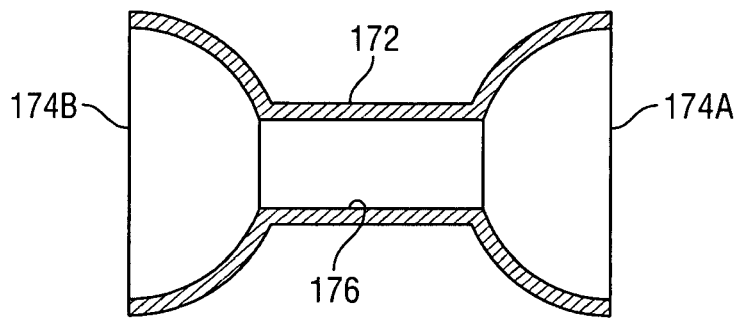
Figure 4C:
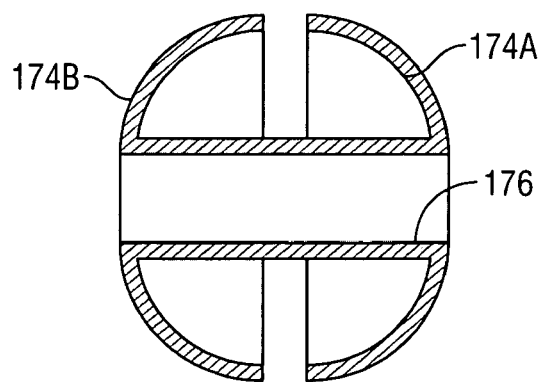

FIGS. 4B and 4C illustrate another conduit 170 which may be deployed to fluidly connect the lung with an extrapleural airway. The conduit 170 includes a body 172 and an end portion 174A, B extending from each end of the body. A passageway 176 extends through the conduit. The end portions 174A, B are bowl-shaped in this example and are configured such that they may be inverted. Both end portions are shown inverted in FIG. 4C. The invertible end portions thus can sandwich tissue when the conduit is positioned at a target site. Also, the conduit may be elastomeric to provide increased resilience and compression of the sandwiched tissue layers such that side flow and leakage around the conduit is minimized.

FIGS. 5A-5C illustrate another conduit in accordance with the present invention having a center section 208 and at least one extension member (or finger) 202 extending from each end of the center section. The extension members, as will be discussed in more detail below, are capable of deflecting or outwardly bending to secure the conduit in an opening created in an airway wall thereby maintaining the patency of the opening. The extension members may deflect such that opposing extension members may form a V, U, C, horseshoe, or other type of shape when viewed from the side.

Additionally, the conduits shown in FIGS. 5A-5C include a center-control segment 235 which restricts or limits radial expansion of the center section. The center-control segments are adapted to straighten as the center section is radially expanded. Once the center-control segments become straight or nearly straight, radial expansion of the conduit is prevented. In this manner, the radial expansion of the conduit may be self controlled.

The conduits described herein may have various states (configurations or profiles) including but not limited to (1.) an undeployed state and (2.) a deployed state.

The undeployed state is the configuration of the conduit when it is not secured in an opening in an airway wall and, in particular, when its extension members (or fingers) are not outwardly deflected to engage the airway wall. FIG. 5A is a side view of a conduit 200 in an undeployed state. As shown in this figure, extension members 202A, 202B extend straight from the ends 210, 212 respectively of center section 208. The extension members shown in this example are parallel. However, the invention is not so limited and the extension members need not be parallel.

The deployed state is the configuration of the conduit when it is secured in a channel created in an airway wall and, in particular, when its extension members are outwardly bent to engage the airway wall such that the conduit is fixed in the opening. An example of a conduit in its deployed configuration is shown in FIGS. 5B and 5C. FIG. 5B is a side view of a conduit in its deployed state and FIG. 5C shows a front view of the conduit of FIG. 5B.

As shown in FIGS. 5A-5C, the conduit includes a center section 208 having a short passageway. This center section may be a tubular-shaped open-frame (or mesh) structure having a plurality of ribs. As discussed herein, a cover, coating or barrier may be coaxially disposed around the frame. Alternatively, the center section may be a sheet of material rolled or folded into shape.

The axial length of the center section or passageway may be relatively short. In FIGS. 5A-5C, the passageway's length is about equal to the width of a wire segment or rib. Here, the center section serves as a bridge or junction for the extension members and it is not required to be long. The axial length of the passageway may therefore be less than 1 mm and even approach 0 mm. In one example, the length of the center section is less than twice the square root of a cross sectional area of the center section. However, the center section may also have passageways which have lengths greater than 1 mm.

Indeed, when the conduit is used to place the lung and the trachea in fluid communication, and when the lung is not in contact with the trachea, the center section may have a length of 0.5-50 mm and perhaps 5-10 mm.

The overall length (L) of the conduit may be distinguished from the length of the center section because the overall length includes the lengths of the extension members. Further, the overall length (L) is dependent on which state the conduit is in. The overall length of the conduit will typically be shorter when it is in a deployed state as shown in FIG. 5B than when it is in an undeployed state as shown in FIG. 5A. The overall length (L) for a deployed conduit may be less than 6 mm and perhaps, between 1 and 20 mm.

FIG. 5C shows a front view of the conduit 200 shown in FIG. 5B. FIG. 5C shows the passageway having a hexagonal (or circular) cross section. The cross-section, however, is not so limited: The cross section may be circular, oval, rectangular elliptical, or any other multi-faceted or curved shape. The inner diameter ($D_1$) of the center section, when deployed, may range from 1 to 10 mm and perhaps, from 2 to 5 mm. Moreover, in some variations, the cross-sectional area of the passageway, when deployed, may be between 0.2 $mm^2$ to 300 $mm^2$ and perhaps between 3 $mm^2$ and 20 $mm^2$.

As mentioned above, extending from the ends of the center section 208 are extension members 202A, 202B which, when the conduit is deployed, form angles A1, A2 with a central axis of the passageway. When viewed from the side such as in FIG. 5B, opposing extension members may have a V, U, C, horseshoe or other shape. The extension members 202A, 202B may thus outwardly rotate until they sandwich tissue between opposing extension members.

The angles A1, A2 may vary and may range from, for example, 30 to 150 degrees, 45 to 135 degrees and perhaps from 30 to 90 degrees. Opposing extension members may thus form angles A1 and A2 of greater than 90 degrees when the conduit is deployed in a channel. For example, angles A1 and A2 may range from 90 to 125 degrees when the conduit is deployed. The greater angles tend to sandwich the pleural tissue layers between the opposing extension members preventing gas from entering the pleural space. However, the conduits of the present invention are not so limited and the angles may be further increased or decreased.

Moreover, the angle A1 may be different than angle A2. Accordingly, the conduit may include proximal extension members which are parallel (or not parallel) to the distal extension members. Additionally, the angle corresponding to each proximal extension member may be different or identical to that of another proximal extension member. Likewise, the angle corresponding to each distal extension member may be different or identical to that of another distal extension member.

The extension members may have a length between 1 and 20 mm and perhaps, between 2 and 6 mm. Also, with reference to FIG. 5C, the outer diameter ($D_2$) of a circle formed by the free ends of the extension members may range from 2 to 20 and perhaps, 3 to 10 mm. However, the dimensions disclosed above are provided as examples and the invention is not intended to be limited to only the scope of the examples. Further, the length of the distal extension members may be different than the length of the proximal extension members. The length of the distal extension members may be, for example, longer than that of the proximal extension members. Also, the lengths of each proximal extension member may be different or identical to that of the other proximal extension members. Likewise, the lengths of each distal extension member may be different or identical to that of the other distal extension members.

The number of extension members on each end of the center section may also vary. The number of extension members on each end may range from 2-20 and perhaps, 3-10 or 6-10. Also, the number of proximal extension members may differ from the number of distal extension members for a particular conduit. Moreover, the extension members may be symmetrical or non-symmetrical about the center section. The proximal and distal extension members may also be arranged in an in-line pattern or an alternating pattern. The extension members may also have openings to permit tissue ingrowth for improved retention.

The shape of the extension members may also vary. They may be open-framed and somewhat petal-shaped as shown in FIGS. 5A-5C. In these figures, the extension members 202A, 202B comprise wire segments or ribs that define openings or spaces between the members. However, the invention is not so limited and the extension members may have other shapes. The extension members may, for example, be solid or they may be filled.

The conduit may be constructed to have a low profile delivery state. The delivery state is the configuration of the conduit when it is being delivered through an airway or a working channel of a bronchoscope, endoscope, or other delivery tool. The maximum outer diameter of the conduit in its delivery state must therefore be such that it may fit within the delivery tool, instrument, or airway.

In one variation, the conduit has a small diameter when in its delivery state and is radially expandable such that it may be radially expanded to a larger size upon deployment. For example, the conduit may be sized for insertion into a bronchoscope having a 2 mm or larger working channel. Upon deployment, the conduit may be expanded to an increased internal diameter (e.g., 3 mm.) However, the invention is not limited to such dimensions. It is contemplated that the conduits 200 may have center sections that are expanded into a larger profile from a reduced profile, or, the center sections may be restrained in a reduced profile, and upon release of the restraint, return to an expanded profile.

Additionally, the conduit need not have a smaller delivery state. In variations where the center section is not able to assume a second smaller delivery profile, a maximum diameter of the first or deployed profile will be sufficiently small such that the conduit may be placed and advanced within an airway or a working channel of a bronchoscope or endoscope. Also, in cases where the conduit is self-expanding, the deployed shape may be identical to the shape of the conduit when the conduit is at rest or when it is completely unrestrained.

The conduit 200 shown in FIGS. 5A-5C also includes diametric-control segments, tethers, or leashes 235 to control and limit the expansion of the center section 208 when deployed. This center-control segment 235 typically is shaped such that when the conduit radially expands, the center-control segment bends until it is substantially straight or no longer slack. Such a center-control segment 235 may be circular or annular shaped. However, its shape may vary widely and it may have, for example, an arcuate, semi-circular, V, or other type of shape which limits the expansion of the conduit.

Typically, one end of the center-control segment is attached or joined to the center section at one location (e.g., a first rib) and the other end of the center-control segment is connected to the center section at a second location (e.g., a rib adjacent or opposite to the first rib). However, the center-control segments may have other constructs. For example, the center-control segments may connect adjacent or non-adjacent center section members. Further, each center-control segment may connect one or more ribs together. The center-control segments may further be doubled up or reinforced with ancillary control segments to provide added control over the expansion of the center section. The ancillary control segments may be different or identical to the primary control segments.

FIG. 5B illustrates the conduit 200 in its deployed configuration. As discussed above, the center-control segments 235 may bend or otherwise deform until they maximize their length (i.e., become substantially straight) such as the center-control segments 235 shown in FIG. 5B. However, as discussed above, the invention is not so limited and other types of center-control segments may be employed.

The control segments, as with other components of the conduit, may be added or mounted to the center section or alternatively, they may be integral with the center section. That is, the control segments may be part of the conduit rather than separately joined to the conduit with adhesives or welding, for example. The control segments may also be mounted exteriorly or interiorly to the members to be linked.

Additionally, sections of the conduit may be removed to allow areas of the conduit to deform more readily. These weakened areas provide another approach to control the final shape of the deployed conduit. Details for creating and utilizing weakened sections to control the final shape of the deployed conduit may be found in U.S. Ser. No. 09/947,144 filed on Sep. 4, 2001.

The conduit described herein may be manufactured by a variety of manufacturing processes including but not limited to laser cutting, chemical etching, punching, stamping, etc. For example, the conduit may be formed from a tube that is slit to form extension members and a center section between the members. One variation of the conduit may be constructed from a metal tube, such as stainless steel, 316L stainless steel, titanium, titanium alloy, nitinol, MP35N (a nickel-cobalt-chromium-molybdenum alloy), etc. Also, the conduit may be formed from a rigid or elastomeric material that is formable into the configurations described herein. Also, the conduit may be formed from a cylinder with the passageway being formed through the conduit. The conduit may also be formed from a sheet of material in which a specific pattern is cut. The cut sheet may then be rolled and formed into a tube. The materials used for the conduit can be those described above.

Additionally, the conduits described herein may be comprised of a shape memory alloy, a super-elastic alloy (e.g., a NiTi alloy), a shape memory polymer, a polymeric material, an implantable material, a material with rigid properties, a material with elastomeric properties, or a combination thereof. The conduit may be constructed to have a natural self-assuming deployed configuration, but is restrained in a pre-deployed configuration. As such, removal of the restraints causes the conduit to assume the deployed configuration. A conduit of this type could be, but is not limited to being, comprised from a shape memory alloy. It is also contemplated that the conduit could comprise a shape memory alloy such that, upon reaching a particular temperature (e.g., 98.5° F.), it assumes a deployed configuration.

Also, the conduit described herein may be formed of a plastically deformable material such that the conduit is expanded and plastically deforms into a deployed configuration. The conduit may be expanded into its expanded state by a variety of devices such as, for example, a balloon catheter.

FIG. 7A illustrates another variation of a conduit 200 having a tissue barrier 240. The tissue barrier 240 prevents tissue ingrowth from occluding the channel or passage of the conduit 200. The tissue barrier 240 may coaxially cover the center section from one end to the other or it may only cover one or more regions of the conduit 200. The tissue barrier may completely or partially cover the conduit. The tissue barrier 240 may be located about an exterior of the conduit's surface, about an interior of the conduit's surface, or the tissue barrier 240 may be located within openings in the wall of the conduit's surface. Furthermore, in some variations of the invention, the center section 208 itself may provide an effective barrier to tissue ingrowth. The tissue barrier, of course, should not cover or block the entrance and exit of the passageway such that air is prevented from passing through the conduit's passageway. However, in some constructs, the tissue barrier may partially block the entrance or exit of the passageway so long as air may continue to pass through the conduit's passageway.

The tissue barrier may be formed from a material, or coating that is a polymer or an elastomer such as, for example, silicone, polyurethane, PET, PTFE, or expanded PTFE. Moreover, other biocompatible materials will work, such as a thin foil of metal, etc. The coatings may be applied, for example, by either dip coating, molding, spin-coating, transfer molding or liquid injection molding. Or, the tissue barrier may be a tube of a material and the tube is placed either over and/or within the conduit. The tissue barrier may then be bonded, crimped, heated, melted, shrink fitted to the conduit. The tissue barrier may also be tied to the conduit with a filament of, for example, a suture material. The tissue barrier may also be placed on the conduit by either solvent swelling applications or by an extrusion process. Also, a tissue barrier may be applied by either wrapping a sheet of material about the conduit, or by placing a tube of the material about the conduit and securing the tube to the conduit. Likewise, a tissue barrier may be secured on the interior of the conduit by positioning a sheet or tube of material on the inside of the center section and securing the material therein.

FIGS. 7B and 7C respectively illustrate a side view and a front view of another conduit 300 having a partial tissue barrier coating. The conduit 300 includes a center section 310, a plurality of extension members 320, and a partial tissue barrier 330. The conduit 300 is thus different than that shown in FIG. 7A in that the center section is longer and that the tissue barrier 330 only partially covers the extension members 320. In particular, the center section 310 shown in FIGS. 7B-7C is cylindrical or tubular-shaped. This shape may be advantageous when a relatively longer passageway is desired. Also, it is to be understood that the overall (or three dimensional) shape of the center section, when deployed, is not limited to the shape shown here. Rather, it may have various shapes such as, for example, rectangular, tubular, conical, hour-glass, hemi-toroidal, etc.

Additionally, the tissue barrier 330 covers only a proximal region 350 of the extension members and leaves a distal region 340 of the extension members uncovered. The distal region 340 of the extension members 320 is shown as being open-framed. However, the invention is not so limited. The distal region of the extension members may be solid and it may include indentations, grooves, and recesses for tissue ingrowth. Also, the extension members may include small holes for tissue ingrowth. For example, the distal region of the extension members may have a dense array of small holes. In any event, the conduits described herein may include at least one region or surface which is susceptible to tissue ingrowth or is otherwise adherent to the tissue. Accordingly, tissue ingrowth at the distal region 340 of the extension members is facilitated while tissue growth into the passageway 325 is thwarted.

As shown in FIG. 7D, tissue growth 360 into the uncovered region 340 further secures the extension members to the tissue wall 370. The distal region of the extension members may also include tissue growth substances such as epithelial growth factors or agents to encourage tissue ingrowth. Accordingly, conduit 300 may be configured to engage the tissue wall 370 as well as to allow tissue to grow into predetermined regions of the conduit.

The conduit shown in FIG. 7A also includes a visualization ring or marker 242. The marker 242 is visually apparent during a procedure. The marker is observed as the conduit is placed in a collateral channel and, when the marker is even with the opening of the channel, the conduit may be deployed. In this manner, the visualization feature facilitates alignment and deployment of the conduits into channels.

The visualization ring or mark may be a biocompatible polymer and have a color such as white. Also, the visualization feature may protrude from the center section or it may be an indeniation(s). The visualization mark may also be a ring, groove or any other physical feature on the conduit. Moreover, the visualization feature may be continuous or comprise discrete segments (e.g., dots or line segments).

The visualization feature may be made using a number of techniques. In one example, the mark is a ring formed of silicone and is white. The polymeric ring may be spun onto the tissue barrier. For example, a clear silicone barrier may be coated onto the conduit such that it coaxially covers the extension members and the center section as shown in FIG. 7A. Next, a thin ring of white material such as a metal oxide suspended in clear silicone may be spun onto the silicone coating. Finally, another coating of clear silicone may be applied to coat the white layer. The conduit thus may include upwards of 1-3 layers including a tissue barrier, a visualization mark layer, and a clear outer covering.

The shape of the visualization mark is not limited to a thin ring. The visualization mark may be large, for example, and cover an entire half of the conduit as shown in FIG. 7B. The visualization mark may, for example, be a white coating disposed on the proximal or distal half of the conduit. The visualization mark thus may extend from an end of the extension members to the center section of the conduit. As explained in more detail below, when such a device is deposited into a channel created in lung tissue, the physician may observe when one-half of the conduit extends into the channel. This allows the physician to more accurately position and deploy the conduit.

Multiple visualization marks or features may be incorporated on the conduit. For example, an elongated conduit may have one proximal visualization ring and one distal visualization ring to identify the proximal and distal end portions of the conduit during a surgical procedure.

The visualization member is made visually apparent for use with, for example, an endoscope. The visualization feature, however, may also be made of other vision-enhancing materials such as radio-opaque metals used in x-ray detection. It is also contemplated that other elements of the conduit can include visualization features such as but not limited to the extension members, tissue barrier, control segments, etc.

The conduits may also include a one-way valve. The valve may be positioned such that it permits expiration of gas from lung tissue but prevents gas from entering the tissue. The valve may be placed anywhere within the passageway of the conduit. The valve may also be used as bacterial in-flow protection for the lungs. The valve may also be used in conjunction with a tissue barrier and the tissue barrier may be disposed coaxially about the conduit. Various types of one way valves may be used as is known to those of skill in the art.

The conduits described herein may also include modified surfaces that prevent the channel from closing by reducing tissue growth into the passageway. The modified surfaces may prevent the conduit from being ejected from the channel as the wound heals. The surfaces of the conduit may be modified, for example, by depositing a bioactive substance or medicine onto the exterior surface of the conduit.

The bioactive substances are intended to interact with the tissue of the surgically created channels. These substances may interact with the tissue in a number of ways. They may, for example, accelerate wound healing such that the tissue grows around the exterior surface of the conduit and then stops growing; encourage growth of the epithelial or endothelial cells; inhibit wound healing such that the injury site (e.g., the channel or opening) does not heal leaving the injury site open; and/or inhibit infection (e.g., reduce bacteria) such that excessive wound healing does not occur which may lead to excessive tissue growth at the channel thereby blocking the passageway. However, the foregoing statements are not intended to limit the present invention and there may be other explanations why certain bioactive substances have various therapeutic uses in the lung tissue. Again, the bioactive substances are intended to prevent the implant from being ejected as well as prevent the lung tissue from filling or otherwise blocking the passageway of the conduit.

A variety of bioactive substances may be used with the devices described herein. Examples of bioactive substances include, but are not limited to, pyrolitic carbon, titanium-nitride-oxide, paclitaxel, fibrinogen, collagen, thrombin, phosphorylcholine, heparin, rapamycin, radioactive 188Re and 32P, silver nitrate, dactinomycin, sirolimus, cell adhesion peptide. Again, other substances may be used with the conduits such as those substances which affect the wound healing response (or rate) of injured lung tissue.

Figure 8:
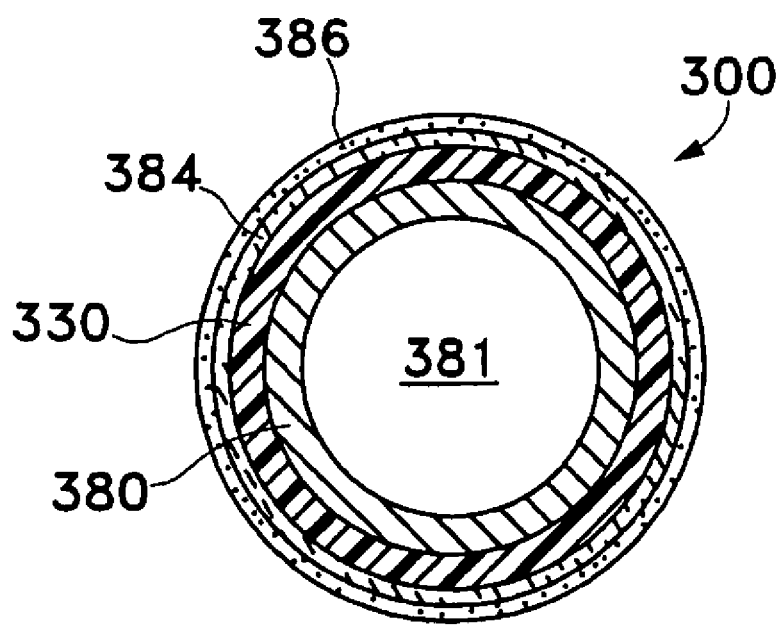
FIG. 8 is a cross sectional view of the conduit shown in FIG. 7B taken along line A-A.

A cross section of a conduit 300 having a modified surface is shown in FIG. 8. In particular, the conduit 300 comprises an inner frame layer or ribs 380 which define a passageway 381 for air to flow through. Coaxially surrounding the frame 380 is a tissue barrier 330. Additionally a visualization coating 384 is disposed on the tissue barrier 330. The visualization coating 384 is deposited as described above. A bioactive substance 386 is deposited on the visualization layer either directly or via a binding layer as described below. In this manner, the bioactive substance is disposed on an exterior surface of the conduit and contacts tissue when the device is deployed in a channel. However, it is contemplated that the conduits may include additional layers such as, for example, an additional silicone layer over the visualization layer. Also the order of the layers may be different than that described above. Also, not all coatings and materials shown in FIG. 8 are necessary to carry out the present invention.

The bioactive layer may also serve as the visualization coating or tissue barrier in some instances. For example, silicone and one or more bioactive substances may be mixed together and disposed on the conduit as a single coating. The single integral layer may serve both to physically and chemically prevent tissue from filling the conduit's passageway. It may also be visually apparent during a procedure.

The bioactive substances may be deposited on the exterior surface of the conduit evenly or in discrete (intermittent) amounts. The thickness of the coatings may be uniform or the thickness may vary across certain regions of the conduit. This may provide higher therapeutic doses corresponding to certain regions of the injury site. For example, it may be desirable to provide a higher concentration of a bioactive substance near the ends of the conduit rather than in the center section.

The bioactive coatings may be selectively applied by spraying the bioactive substance onto uncovered regions of the conduit. For example, the bioactive substances may be disposed on at least a portion of the tissue barrier or the open-frame (or mesh) structure itself. The substances may also be applied by dipping, painting, printing, and any other method for depositing a substance onto the conduit surface. Additionally, binding materials may be applied to the exterior surface of the conduit upon which the bioactive agents may be deposited. Cross-linked polymers and or biodegradable polymers such as, for example, chondroitin sulfate, collagen and gelatin may be applied to the exterior surface of the conduit prior to depositing the bioactive substances. Additionally, the exterior surface of the conduit may be treated via etching processes or with electrical charge to encourage binding of the bioactive substances to the conduit.

Again, the bioactive substances herein described are deposited on the exterior of the conduits to, amongst other things, prevent ejection of the conduit from the injury site. The bioactive substances also serve to reduce or impede tissue growth into the conduit's passageway. In this manner, the conduits maintain the patency of channels surgically created in intrapleural and extrapleural airways allowing air to pass therethrough.

Figure 9A:
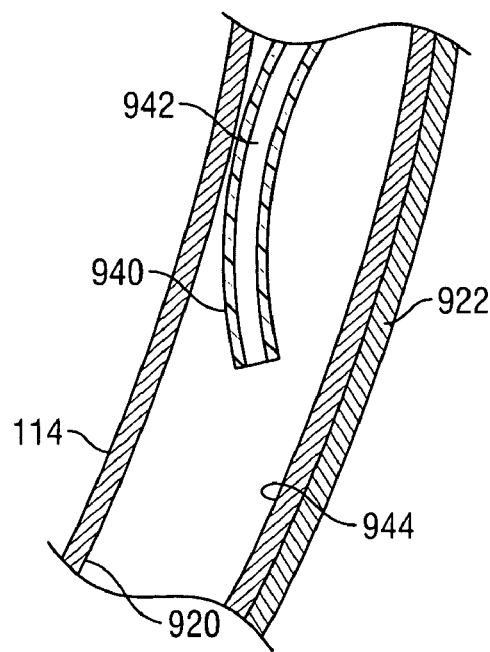
Figure 9B:
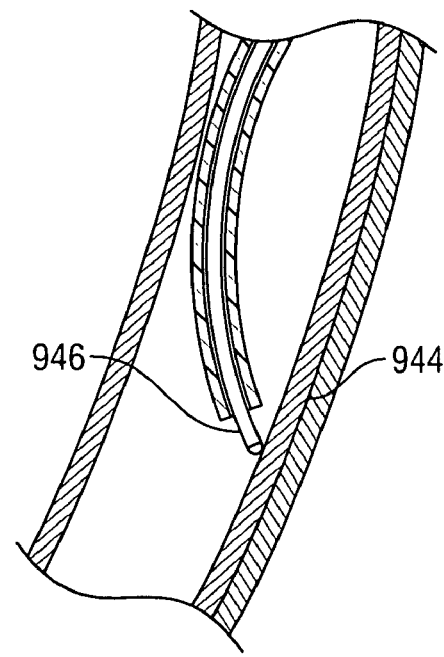

FIGS. 9A-9G illustrate a method of deploying a conduit in accordance with the present invention. FIG. 9A illustrates the advancement of an access device 940 into an airway such as the trachea 920. The access device 940 includes at least one lumen or working channel 942. The access device 940 locates an approximate site 944 for creation of a channel. A bronchoscope or other similar type of endoscope may be used as the access device 940. In cases where the access device 940 is a bronchoscope or similar device, the access device 940 is equipped so that the surgeon may observe the site for creation of the channel in the trachea wall. FIG. 9B illustrates a blood vessel detection device 946 advanced through the channel 942 of the access device 940 towards the site 944. An example of a blood vessel detection device is described in U.S. Ser. No. 10/080,344 filed Feb. 21, 2002 which is hereby incorporated by reference in its entirety. The site 944 is inspected to determine whether a blood vessel is adjacent to the site. It is generally desirable to avoid blood vessels when creating a channel in the tissue walls. The step shown in FIG. 9B is desirable but not necessary to carry out the present invention.

Figure 9C:
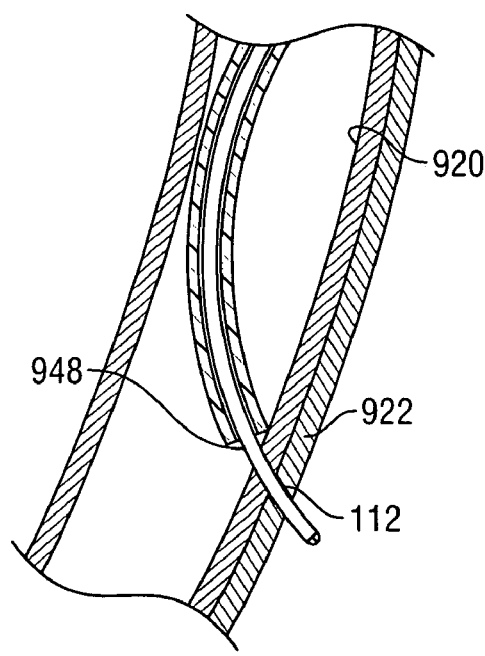

FIG. 9C illustrates the creation of a channel 112 by a hole-making device 948. Examples of hole-making devices 948 are disclosed in U.S. Ser. No. 10/079,605 filed Feb. 21, 2002. Furthermore, variations of this invention include the use of devices which are equipped for both detection and hole-making. Examples of such devices are disclosed in U.S. Ser. No. 09/946,706 filed Sep. 4, 2001 and U.S. Ser. No. 10/080,344 filed Feb. 21, 2002.

As shown in FIG. 9C, the device 948 may be manipulated to a position that is optimal for creation of the collateral channel 112. It is noted that the access device or the hole-making device may be steerable. Such a feature assists in positioning any of the devices used in the inventive method. It is also noted that the hole-making device may emit radio frequency energy from its tip to create the hole in the trachea wall 920. The hole-making device is further urged into contact with the lung wall 922. Energy is applied until the device has created a channel through both walls 920, 922. Alternatively, the hole-making device may feature a needle-type structure which is punched through each of the above mentioned walls.

Additionally, it is contemplated that during the procedures described herein the lung opposite the lung being treated may be isolated and ventilated so that the lung being treated does not carry out gaseous exchange during the procedure. Also, as described above, the tissue layers may be fixed together at the target location prior to creating the channel through the tissue layers. Fixing the tissue layers together prior to creating the channel may reduce the chances that any air may enter the pleural space between the pleural membrane layers.

Figure 9D:
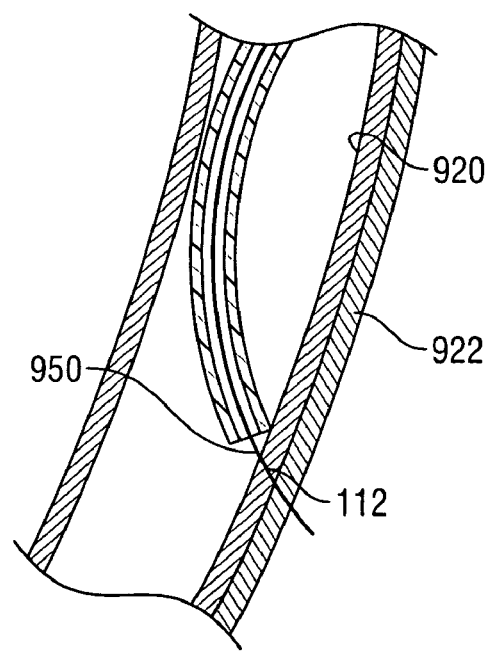

FIG. 9D illustrates another variation of the inventive method in which a guide-member, such as a guide-wire 950, or other similar device, is inserted into the channel 112 extending through the walls of the trachea and the lung. It is noted that the use of a guide-member 950 is optional.

FIG. 9E illustrates the advancement of a catheter device 952 into the channel 112. In the variations using a guide-member 950, the catheter 952 is advanced over the guide-member 950 and into the channel 112. One variation of the inventive method includes the use of a catheter 952 which has a conduit-954 attached thereto. Some examples of the conduit 954 as well as catheter type delivery devices 952 are disclosed throughout this disclosure. If the conduit 954 is of the type that is not self-expanding, the catheter 952 may also be configured to expand the conduit 954 within the collateral channel 112.

FIG. 9F illustrates deployment of the distal portion of the conduit. In particular, FIG. 9F shows deployment of distal extension members 956. Deploying the distal portion of the conduit prior to deploying the proximal portion of the conduit may be desirable because the deployed distal portion may serve as a grapple. Once the distal portion is deployed, the assembly may be urged proximally or rearwards to compress the tissue walls together. The proximal portion of the conduit may then be deployed to complete deployment of the conduit. However it is to be understood that the conduit may be deployed in various manners and the method of deployment may depend on the type of conduit deployed. For example, as will be described in more detail below, a balloon member may be actuated to deploy opposing extension members or deflectable fingers simultaneously such that the tissue walls are sandwiched between the opposing extension members.

Finally, FIG. 9G illustrates the conduit 954 placed within the channel such that the trachea 920 is fluidly connected with the lung 924 to allow air to directly pass from the parenchymal tissue 924 to the trachea. FIG. 9G also shows the withdrawal of the guide-member 950, catheter 952, and the access device 940. As shown by the arrows of FIG. 9G, the conduit 954 provides a passageway for trapped non-functional air to be evacuated from a hyper-inflated lung.

As stated above, this method and device may also include use of an adhesive or bioactive material disposed around the conduit to prevent air from leaking around the conduit's passageway. Adhesives, bioactive materials and other substances may be applied to the channel before or after delivery of the conduit. The substance may be applied or deposited using, for example, a delivery catheter having at least one lumen. The delivery catheter may be manipulated to the site through access device 940 or by another means as is known to those of ordinary skill in the art. Once the catheter is positioned the adhesives may be ejected to the target site to coat the interior wall of the channel.

It is noted that a variation of the inventive method includes using a guide-wire to create the channel through the tissue walls and leaving the guide-wire, to extend through the channel. Accordingly, a conduit may be advanced over the guide-wire into the collateral channel.

It is also to be understood that though the above procedure describes deploying the conduit from the trachea to the lung, the invention also includes deploying the conduit in a different direction or manner. That is, the conduit may be deployed from the parenchymal tissue of the lung to the trachea. In the case that the conduit is deployed from the parenchyma to the trachea, the access device must be manipulated deep into the lung until a target site is selected. The procedure may then be carried out similarly to that described above except that the initial target site is the lung wall. Consequently, the hole-making device must penetrate the lung wall prior to penetrating the trachea wall. In either case, however, the trachea may be placed in fluid communication with the lung via the deployed conduit.

Figure 10A:
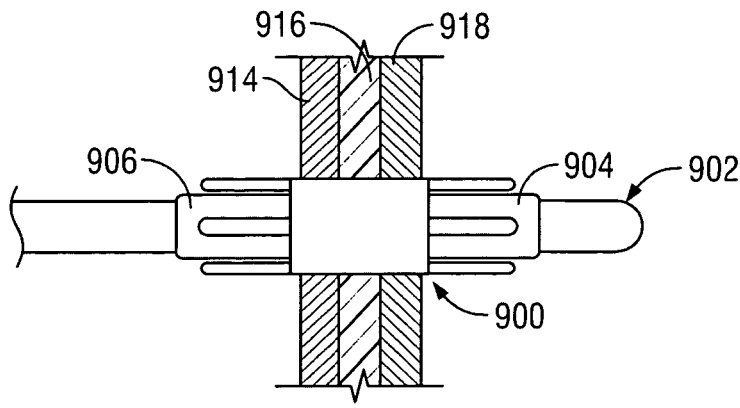
FIGS. 10A to 10D illustrate an enlarged cross sectional view of a conduit being deployed in a channel extending through multiple layers of tissue using an inflatable member.

FIGS. 10A-10D show an enlarged view of one technique for deploying a conduit 900 to fluidly connect the trachea and the lung using an inflatable member. FIG. 10A illustrates the conduit 900 being delivered into a channel formed in the trachea 914, the parietal pleura 916, and the visceral pleura 918. The conduit is shown being delivered via a balloon catheter 902. The conduit 900 may be attached to the delivery device 902 using the natural resiliency of the conduit 900. Or, in those cases where the conduit is spring loaded, the conduit 900 is restrained in a reduced profile and may be removably affixed to the delivery device 902 using an adhesive, or a removable sleeve such as a heat shrink tube. In this example, the balloon catheter 902 has several balloons including a distal balloon 904, a proximal balloon 906, and a center balloon (not illustrated in FIG. 10A).

Figure 10B:
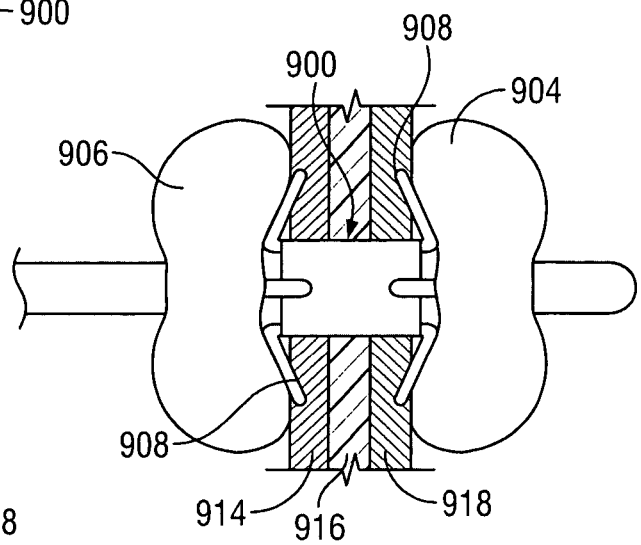

FIG. 10B illustrates the inflation of the distal 904 and proximal 906 balloons to situate the extension members 908. Accordingly, the extension members 908 form a flange or collar about the tissue walls. These opposing extension members sandwich the tissue walls and secure the conduit in place. The balloons 904, 906 may be inflated simultaneously, or in a desired sequence. Deployment of the balloons 904, 906 may also serve to center the conduit 900 in the channel.

Figure 10C:
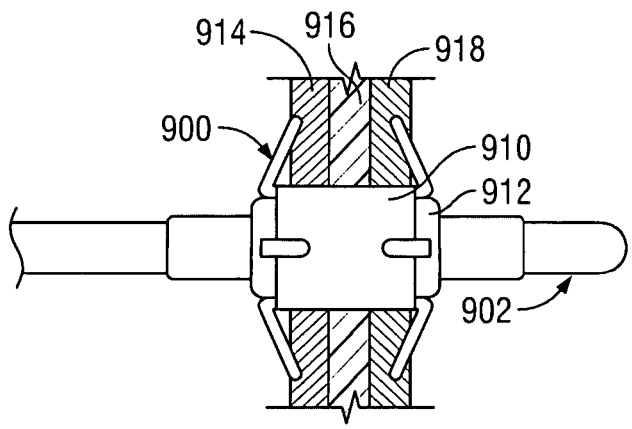

FIG. 10C illustrates inflation of the center balloon 912 which causes expansion of the center section 910 of the conduit 900. If the conduit 900 is affixed to the delivery device 902, expansion of the center balloon 912 causes release of the conduit 900 by release of the adhesive or breaking of the heat shrink tubing (not shown). The attachment may be bioabsorbable and remain in the body, or may remain affixed to the delivery device 902 and is removed with removal of the delivery device 902. Also, it is not necessary for the balloons to be separate. For example, a single balloon may have a pre-set expanded shape or the balloon may be restricted in certain areas to prevent expanding in those areas.

Figure 10D:
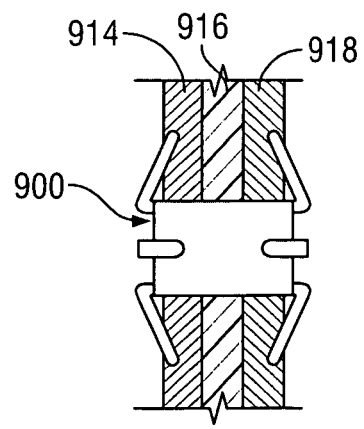

FIG. 10D illustrates the conduit 900 holding the tissue walls together after the delivery device 902 is removed from the site. Another method of deploying a conduit includes restraining the conduit about a delivery device using a wire or string tied in a slip-knot or a series of slip-knots. When the conduit is delivered to a desired location, the proximal end of the wire or string may be pulled which releases the wire/string and deploys the conduit.

It should be noted that deployment of conduits is not limited to that shown above, instead, other techniques may be used to deploy the conduit. For example, spring-loaded or shape memory features may be actuated by mechanical or thermal release and unlocking methods. Additionally, mechanical wedges, lever-type devices, scissors-jack devices, open chest surgical placement and other techniques may be used to deploy the conduit. The conduits may be comprised of an elastic or super-elastic material which is restrained in a reduced profile for deployment and expands to its deployed state upon mechanical actuator or release.

Figure 11A:
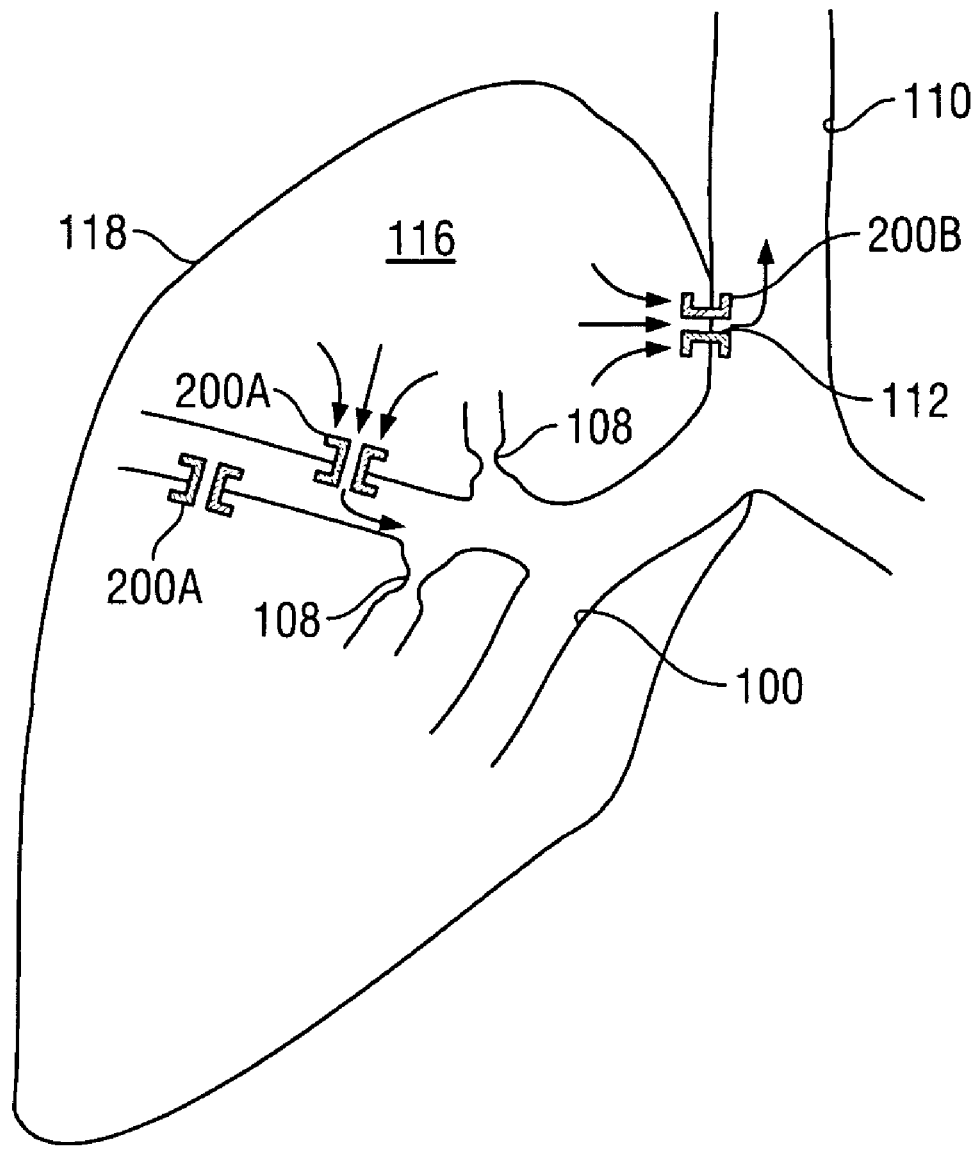
FIGS. 11A-11C depict a lung having both an extra- or transpleural device and an intrapleural device deployed therein to improve gaseous exchange.
Figure 11B:
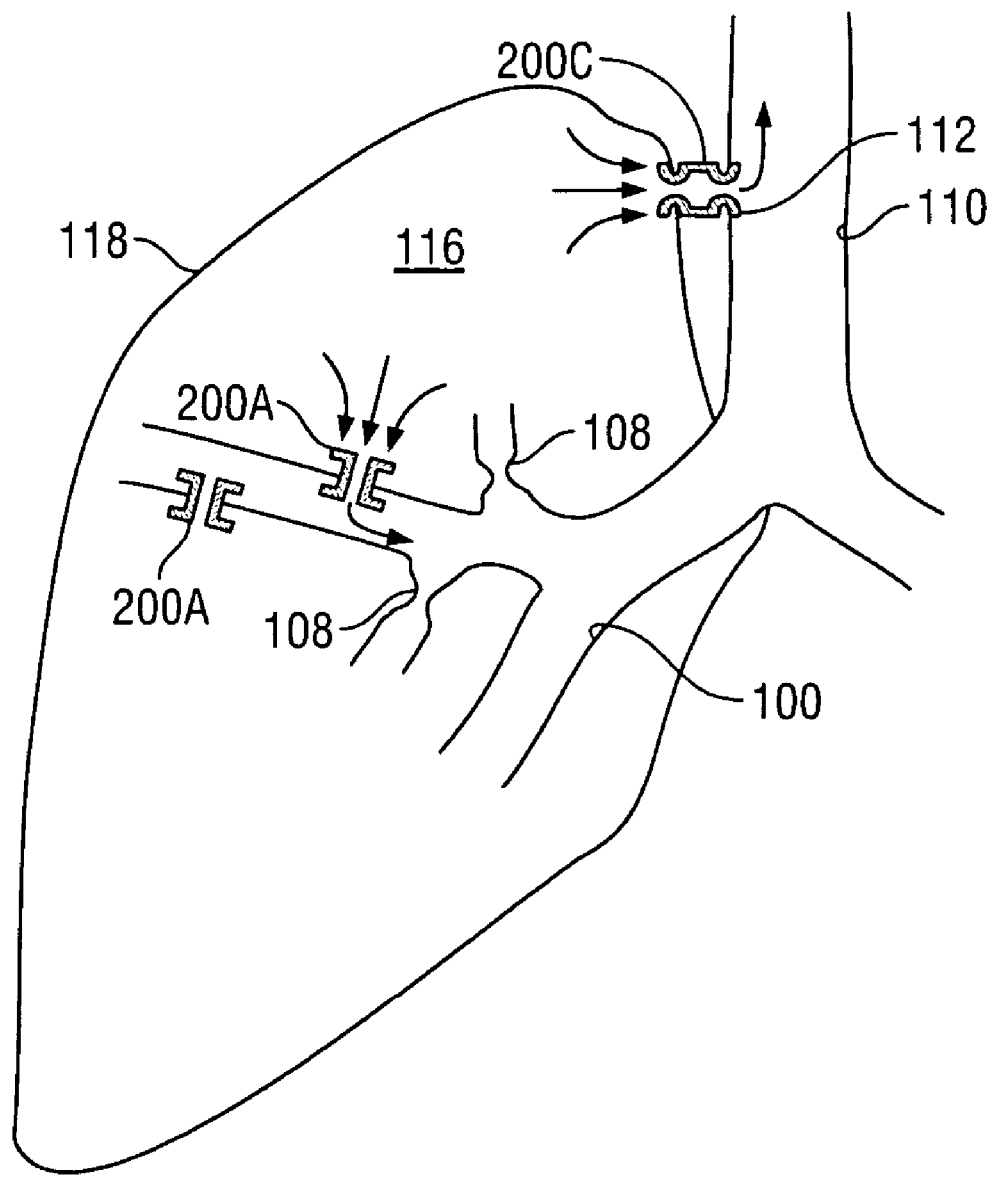
Figure 11C:
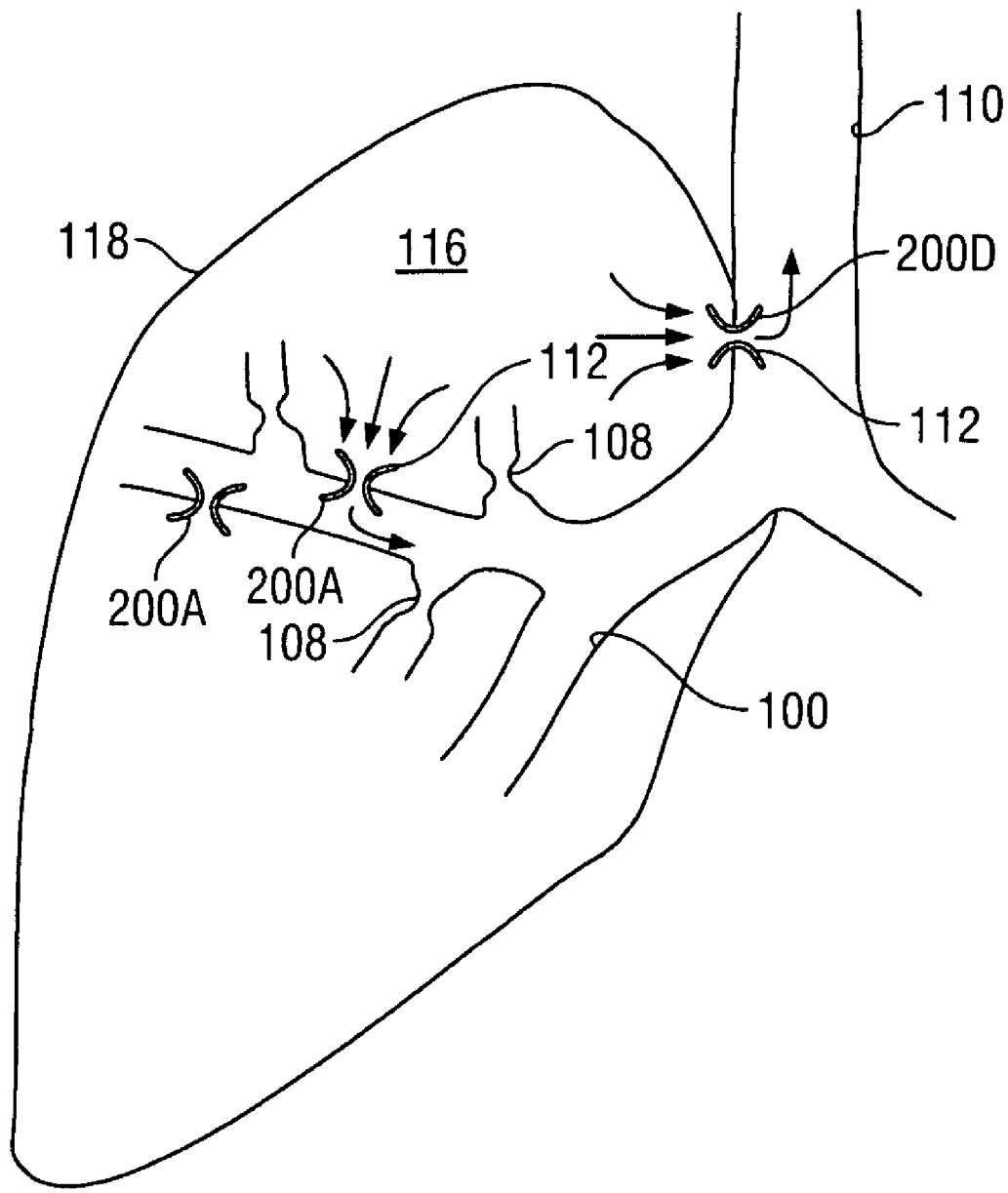

FIGS. 11A-11C illustrate another variation of the present invention which includes deploying a combination of (1.) an intrapleural device and (2.) a transpleural or extrapleural device.

The intrapleural device 200A is deployed in a channel surgically created in an airway within the lung. The conduit 200A maintains the channel's patency allowing trapped non-functional air to pass directly into the airway 100. This improves gas exchange as the air does not have to pass constrictions 108. The intrapleural conduit may be configured identical to the transpleural conduit described above or in some cases, the intrapleural devices may have a shorter center section length. Also, as shown in FIGS. 11A-11C more than one intrapleural device may be deployed in combination with at least one transpleural device. While the invention is not limited to the number of collateral channels which may be created, it is to be understood that 1 or 2 channels may be placed per lobe of the lung and perhaps, 2-12 channels per individual patient. However, as stated above, the invention includes the creation of any number of collateral channels in the lung. This number may vary on a case by case basis. For instance, in some cases in an emphysematous lung, it may be desirable to place 3 or more channels (e.g., intrapleural or transpleural passageways) in one or more lobes of the lung.

FIGS. 11A-11C also show a transpleural device deployed between the lung and the trachea. The transpleural conduits are configured as described above and they may take various shapes. For example, FIG. 11A illustrates a grommet shaped conduit 200B. FIG. 11B illustrates an elongated conduit 200C which is especially useful when the lung is not in contact with the trachea or when a relatively large distance between the tissue is desired. FIG. 11C illustrates a conduit 200D having angled end portions. Conduit 200D may be deployed, for example, as described above using a balloon catheter. Also, as in any of the conduit designs, a sealant may be delivered around the periphery of the conduit to prevent side flow or leakage into the chest cavity or pleural space as well as prevent the conduit from being ejected.

To reiterate, one or more conduits may be deployed within the lung to allow nonfunctional air trapped in the parenchyma (and other portions of the lung) to pass directly into a larger airway via one or more intrapleural devices such as conduits 200A. Additionally, one or mote transpleural devices such as conduits 200B, 200C, 200D may be deployed in combination with the intrapleural devices to allow air to pass directly from the lung to an extrapleural airway such as the trachea. In this manner, gaseous exchange in the lung is improved as carbon dioxide rich gas is transported out of the lung allowing healthier lung regions to expand.

Although the foregoing invention has been described in some detail, by way of illustration and example for-purposes of clarity of understanding, it will be readily apparent to those of ordinary skill in the art in light of the teachings of this invention that certain changes and modifications may be made thereto without departing from the spirit or scope of the appended claims. It is also contemplated that combinations of the above described embodiments/variations or combinations of the specific aspects of the above described embodiments/variations are within the scope of this disclosure.

The invention claimed is:

1. A method for altering the gaseous flow pathways within a lung such that gas may pass directly from lung parenchyma to an airway that is located outside of a pleura surrounding the lung, said method comprising:

advancing a device into a portion of said airway that is outside of the pleura;

creating an opening in said airway outside of the pleura with the device;

fluidly coupling said lung parenchyma to the airway through the pleura such that gas may pass directly from the lung parenchyma to the airway and outside of the body wherein the step of fluidly coupling comprises installing a conduit between said lung parenchyma and said airway, said conduit comprising a passageway for gas to flow through.

2. The method of claim 1 wherein said opening is created using one device selected from the group consisting of a mechanical member and a radio frequency energy delivering device.

3. The method of claim 1, wherein said conduit comprises a first portion, second portion and a center section between said first portion and said second portion, said first portion and said second portion being adapted to secure said conduit to said lung pleura and said airway.

4. The method of claim 3 wherein each of said first portion and second portion of said conduit comprises a plurality of extension members which are deflectable such that when said conduit is deployed, said extension members from said first portion substantially oppose said extension members from said second portion such that tissue may be sandwiched therebetween.

5. The method of claim 3 wherein said center section has a length in the range of 0.5 to 50 mm.

6. The method of claim 5 wherein the center section has a length Of 1 mm.

7. The method of claim 4 wherein the extension members form right angles when deployed.

8. The method of claim 4 wherein the extension members form angles between 90 and 135 degrees when deployed.

9. The method of claim 1, further comprising providing a sealant to an exterior surface of the conduit to prevent side flow of gas around the conduit.

10. The method of claim 9 wherein said sealant comprises talc.

11. The method of claim 9 wherein said sealant is fibrin glue.

12. The method of claim 9 wherein said sealant comprises cyanoacrylate.

13. The method of claim 1, wherein the conduit includes a biocompatible coating.

14. The method of claim 13 wherein said coating promotes wound healing.

15. The method of claim 1, further comprising deploying at least one intrapleural conduit to maintain a channel surgically created in an intrapleural airway.

16. The method of claim 1, further comprising detecting blood vessels prior to said step of creating.

17. The method of claim 1, wherein said conduit comprises at least one visualization feature on an exterior surface of said conduit.

18. The method of claim 1, wherein said step of fluidly coupling comprises creating a channel extending through said pleura and into said lung parenchyma.

19. The method of claim 1, further comprising fixing a wall of said airway to a wall of said pleura.

20. The method of claim 19 wherein said creating step is performed subsequent to said fixing said airway wall to said pleura wall.

21. The method of claim 20 wherein said lung wall is the visceral pleura.

22. The method of claim 1, where the airway comprises an extra-pleural airway.

23. The method of claim 22, where the extra-pleural airway comprises an airway selected from the trachea or mainstem bronchus.

24. The method of claim 1, wherein the gas may pass directly from the lung parenchyma, to the airway, through a natural respiratory opening, and outside of the body.

* * * * *